(12) United States Patent
Hoffer

(10) Patent No.: US 8,814,360 B2
(45) Date of Patent: Aug. 26, 2014

(54) PEDIATRIC VISION TEST

(76) Inventor: Kenneth J. Hoffer, Santa Monica, CA (US)

( * ) Notice: Subject to any disclaimer, the term of this patent is extended or adjusted under 35 U.S.C. 154(b) by 390 days.

(21) Appl. No.: 13/365,940

(22) Filed: Feb. 3, 2012

(65) Prior Publication Data

US 2013/0201453 A1 Aug. 8, 2013

(51) Int. Cl.
*A61B 3/02* (2006.01)
*A61B 3/00* (2006.01)
*A61B 3/10* (2006.01)

(52) U.S. Cl.
USPC ........... 351/239; 351/200; 351/205; 351/222; 351/246

(58) Field of Classification Search
USPC ................. 351/239, 200, 201, 205, 246, 222
See application file for complete search history.

(56) References Cited

U.S. PATENT DOCUMENTS

| 3,355,237 | A | 11/1967 | Simpson |
|---|---|---|---|
| 4,824,237 | A | 4/1989 | Ratner et al. |
| 4,854,695 | A | 8/1989 | Lewis |
| 4,859,052 | A | 8/1989 | McFarland et al. |
| 5,054,908 | A | 10/1991 | Katsumi et al. |
| 5,061,059 | A | 10/1991 | Horn |
| 5,880,814 | A | 3/1999 | McKnight et al. |
| 5,946,075 | A | 8/1999 | Horn |
| 6,293,675 | B1 | 9/2001 | Eger |
| 6,402,320 | B1 | 6/2002 | Borchert |
| 6,652,101 | B1 | 11/2003 | Glaser |
| 7,784,948 | B2 | 8/2010 | Nozawa et al. |
| 7,857,450 | B1 * | 12/2010 | Hofeldt .......................... 351/243 |
| 2004/0076942 | A1 | 4/2004 | O'Neil et al. |

FOREIGN PATENT DOCUMENTS

| CN | 101053511 | 10/2007 |
|---|---|---|
| CN | 201290665 | 8/2009 |
| GR | 1005651 | 9/2007 |
| JP | 2009045402 | 3/2009 |

* cited by examiner

*Primary Examiner* — Dawayne A Pinkney
(74) *Attorney, Agent, or Firm* — Karen S. Canady; canady + lortz LLP

(57) ABSTRACT

Disclosed are a method and kit for testing visual acuity in a subject. The examiner displays a test thread at a set distance in front of the subject's face, and then determines whether the subject grabs or looks at the test thread. These steps are repeated using subsequent threads of varying thickness. The smallest thread to which the subject responds is charted as their best VA in standard notation. The visual acuity of a young child can be quantified using standard adult Snellen acuity levels. The device can be used worldwide, as it transcends language barriers, and in a variety of practice settings, including pediatric ophthalmologist offices, general ophthalmologist offices, optometric offices, pediatricians and family doctors who see young children or persons unable to read a conventional Snellen chart and/or verbalize their responses.

20 Claims, 2 Drawing Sheets

PEDIATRIC VISION TEST

BACKGROUND OF THE INVENTION

It is very difficult to test the visual acuity (VA) of small children. It is nearly impossible to test VA in babies. It is definitely not possible to quantify it as we do with adults using the standard Snellen letter testing. The Snellen test is based upon recognizing specific letters of the alphabet. Visual acuity is calculated as the distance at which test is made divided by the distance at which the smallest optotype identified subtends an angle of 5 arcminutes. Small children cannot read the letters so there are Snellen charts made with pictures that subtend corresponding arcs. However these are of no use in children who have not learned to speak.

There remains a need for simple, inexpensive materials and methods for testing the visual acuity of infants, young children and others with limited communication skills.

SUMMARY OF THE INVENTION

The invention provides a method for testing visual acuity in a subject, without requiring the subject to verbally communicate in response. The method comprises: displaying a test thread at a set distance in front of the subject's face; determining whether the subject grabs or looks at the test thread; displaying a subsequent thread at the set distance; determining whether the subject grabs or looks at the subsequent thread; and repeating steps (c) and (d) using subsequent threads of varying thickness. In a typical embodiment, the set distance is 6-20 inches, typically 14 inches. The test and subsequent threads each has a first end, a second end, and the threads range in thickness between 0.01 mm to 15 mm, typically between 0.10 and 1.5 mm, wherein the thickness of each of the threads differs from all other threads by at least 0.01 mm. In some embodiments, the test thread has a thickness of 20.3 mils (1 mm=39.37 mls), to test for 20/20 VA at 14 inches. Visual acuity is determined by the thickness of the threads the subject is able to grab or obviously identify.

In one embodiment, the method further comprises obscuring the first ends of the test and subsequent threads, such as by placing a hand over the first end of each thread, or by suspending the test and subsequent threads from a valance. In a further embodiment, the method comprises varying, along a horizontal axis, the position of the obscured first ends of the test and subsequent threads.

The method can be performed such that the determining of steps (b) and (d) comprise observing whether the subject obviously notices or grabs the threads. In an alternative embodiment, the determining of steps (b) and (d) comprise observing whether the subject looks at the threads. Optionally, the test and subsequent threads are each displayed at one of two possible locations, and the observing is performed by an observer (which can be the test subject) who is blind to the location of the threads.

The invention additionally provides a kit for testing visual acuity in a subject, which subject need not be capable of providing a verbal response. The kit comprises a plurality of threads, each of the threads having a first end, a second end and a thickness of 0.01 mm to 15 mm, typically 0.10-1.5 mm, wherein the thickness of each of the threads differs from all other threads of the plurality by at least 0.01 mm. The kit further comprises one or more gripping means to which one or more of the threads of (a) is affixed at the first end; and instructions for use of the plurality of threads in testing visual acuity in a subject. In one embodiment, the plurality of threads comprises at least 5 threads. In another embodiment, the plurality of threads comprises at least 10 threads. In a typical embodiment, the plurality of threads consists of 5 to 15 threads.

Optionally, each of the threads is affixed to a separate gripping means. In an alternative embodiment, at least two of the threads are affixed to a single gripping means. In some embodiments, the gripping means comprises a loop or a knob. In some embodiments, the gripping means comprises a handle adapted to be concealed within a user's hand. In one embodiment, the kit further comprises a valance, wherein the valance comprises a concealing face and at least two receiving means affixed to the valance behind the concealing face. The receiving means can be adapted to receive the gripping means at the first end of each of the threads of the plurality, whereby the threads are removably suspended from the valance.

The kit of the invention can comprise a plurality of threads, each having one of the following thicknesses: 406 mils, 203 mils, 105.5 mils, 81.2 mils, 71.05 mils, 60.9 mils, 50.75 mils, 40.6 mils, 20.3 mils, 15.225 mils, and 10.15 mils. Alternatively, the kit comprises threads having a range of thicknesses to allow for testing visual acuities of from 20/10 to 20/400, at distances of 6-20 inches from the subject's eyes.

DETAILED DESCRIPTION OF THE INVENTION

Figure 1:
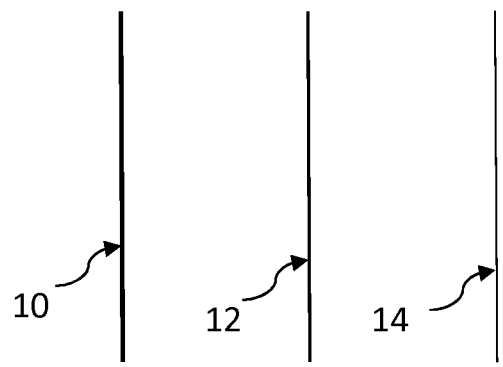
FIG. 1: Schematic illustration of three representative VA test threads of varying relative sizes: large 10, medium 12 and small 14.
Figure 2:
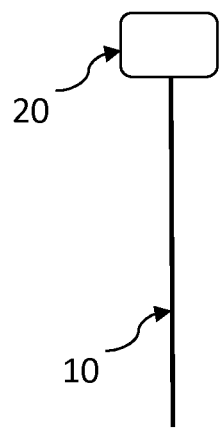
FIG. 2: Schematic illustration of embodiment in which a VA test thread 10 is affixed to a gripping means 20.
Figure 3:
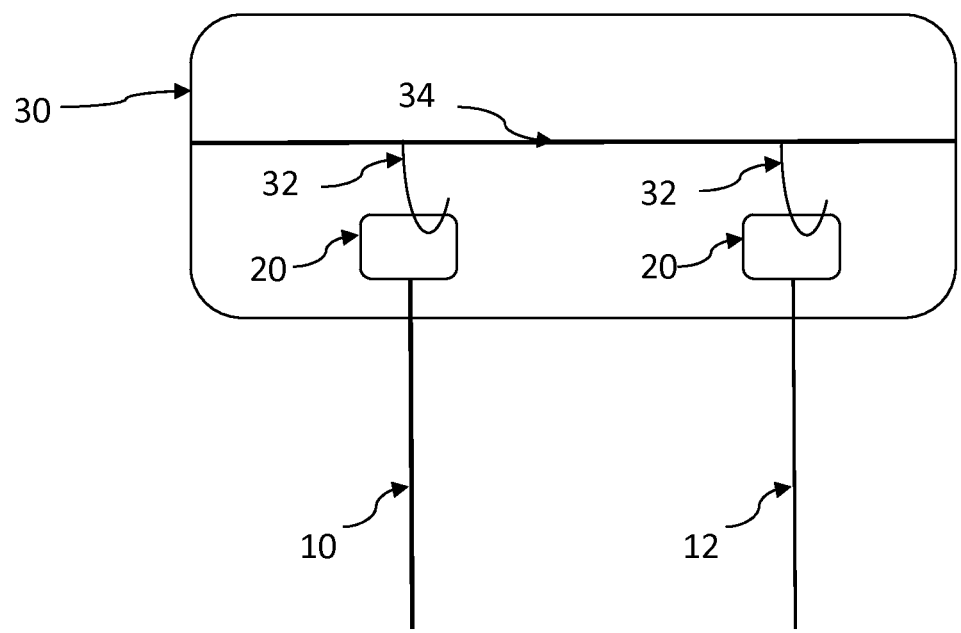
FIG. 3: Schematic illustration of rear view of embodiment that comprises a valance 30, in which VA test threads 10 and 12 are affixed to a gripping means 20, and the gripping means 20 can be suspended from a hook 32 affixed to a support 34 that is part of the valance 30.
Figure 4:
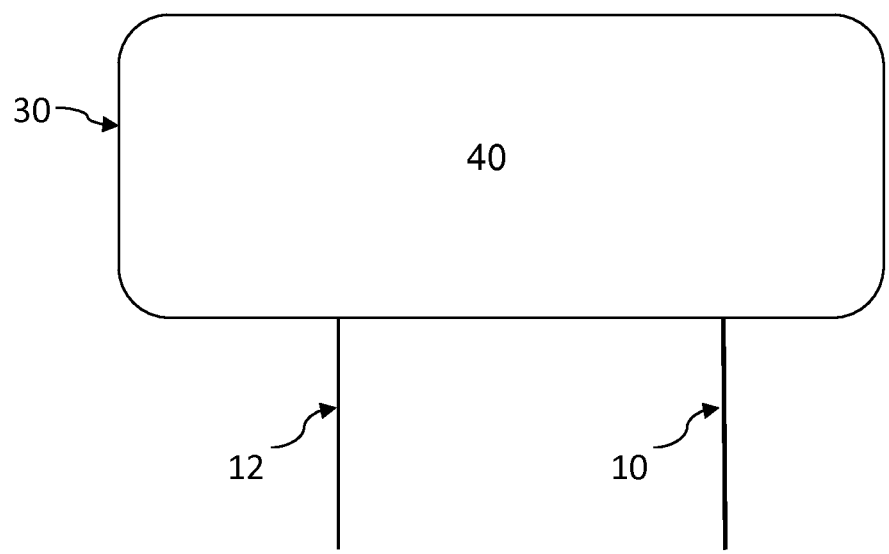
FIG. 4: Schematic illustration of front view of embodiment shown in FIG. 3. When viewed from the front, the concealing face 40 of the valance 30 obscures view of elements that could provide clues as to presence and position of threads 10 and 12.

The invention described herein provides a kit and method for testing visual acuity. In one embodiment, the kit is produced with durable threads 10, 12, 14 that are attached to a gripping means 20, such as a plastic or metal device the examiner would hold. The threads 10, 12, 14 range from a larger mil thickness commensurate with a 20/400 visual acuity (VA), with decreasing thicknesses commensurate with the standard VA levels: 20/200, 20/100, 20/80, 20/70, 20/60, 20/50, 20/40, 20/30, 20/25, 20/20, 20/15 and 20/10, the latter considered the maximum VA of the human eye. Optionally, the gripping means 20 can be labeled with the VA associated with the corresponding thread and set distance. Such labels can be positioned to restrict visibility when desired to avoid observer bias.

To carry out the method, the examiner positions the test thread 10 in front of the subject's face, and determines whether the subject can see it. In some embodiments, the test thread 10 is positioned about 6-8 inches from the subject's eyes, or, in other embodiments, about 10-20 inches from the subject's eyes. In a typical embodiment, the distance between the subject's eyes and the test thread 10 is 14 inches. In all cases, the examiner may implement various methods to camouflage the location or presence of the test thread. At a distance of 14 inches, the thickness of the test thread 10 would be 20.3 mils for a visual acuity of 20/20. For other VA levels, one can determine the appropriate thread thickness using the formula: $VA=0.00145*d/t$, wherein d is distance and t is thickness. Transformed for t: $t=0.00145*d/VA$. For example, when $VA=20/20=1.0$, then $t=0.00145*d$. When $d=14$ in$*0.00145=0.0203$ in=20.3 mils (1 inch=1000 mils 1 mil=1 inch/1000). Thus, the thread thickness to be used at 14 inches from the subject's eye for a VA of 20/40 is 40.6 mils; for a VA of 20/10 the thickness is 10.15 mils; for 20/15 the thickness is 15.225 mils, etc. Those skilled in the art can appreciate other formulations that can be implemented for calculating the relationship between VA and thickness of the test thread.

The device can be presented to the subject so that any handle or gripping means 20 is hidden from the subject in the examiner's hand and the subject can see only the thread 10. If the subject is able to see it, as indicated by the subject's attention to something below the examiner's hand or by their attempt to grab it, the examiner continues to present thinner and thinner threads until the subject no longer indicates awareness that the thread is there. The smallest thread to which the subject responds is charted as their best VA in standard notation.

The method provides a means by which the visual acuity of a young child can be quantified using standard adult Snellen acuity levels. The device can be used worldwide, as it transcends language barriers, and in a variety of practice settings, including pediatric ophthalmologist offices, general ophthalmologist offices, optometric offices, pediatricians and family doctors who see young children or persons unable to read a conventional Snellen chart and/or verbalize their responses.

DEFINITIONS

All scientific and technical terms used in this application have meanings commonly used in the art unless otherwise specified. As used in this application, the following words or phrases have the meanings specified.

As used herein, "durable thread" means a thread strong enough to withstand being repeatedly grabbed at by young children without breaking. Suitable thread material for use in the invention includes, but is not limited to, nylon, polyester, fishing line, cotton, wire, human or animal hair and/or a blend of two or more of the foregoing.

As used herein, "grab" refers to reaching for and/or grasping an object.

As used herein, "looks at" means directs one's visual gaze at. One can ascertain whether a subject looks at a given thread by observing whether the subject's eyes re-direct their gaze to the position of the thread and settles the gaze in that location for a couple of seconds. Alternatively, a subject may be observed to direct their gaze toward the location of a thread but continue to look at other locations near and around the thread in a manner that indicates searching for but not seeing the thread.

As used herein, "a" or "an" means at least one, unless clearly indicated otherwise.

Kit

The invention provides a kit for testing visual acuity in a subject. In a typical embodiment, the kit comprises a plurality of threads 10, 12, 14, each of the threads having a first end, a second end and a thickness of 0.01 mm to 15 mm. In some embodiments, the thickness of the threads ranges from 0.10 mm to 1.5 mm. The thickness of each of the threads differs from all other threads of the plurality by at least 0.01 mm, and in some embodiments, differs by at least 0.10 mm. The kit can, optionally, further comprise one or more gripping means 20 to which one or more of the threads 10, 12, 14 is affixed at the first end, and instructions for use of the plurality of threads in testing visual acuity in a subject. In one embodiment, the plurality of threads comprises at least 5 threads. In another embodiment, the plurality of threads comprises at least 10 threads. In some embodiments, the plurality of threads consists of 5 to 15 threads.

The threads range from a larger mil thickness commensurate with a 20/400 visual acuity (VA), with decreasing thicknesses commensurate with the standard VA levels: 20/200, 20/100, 20/80, 20/70, 20/60, 20/50, 20/40, 20/30, 20/25, 20/20, 20/15 and 20/10, the latter considered the maximum VA of the human eye. In one embodiment, the kit comprises 12 threads, one corresponding to each of the standard VA levels listed. For example, a thread of 20.3 mils thickness, positioned 14 inches in front of a human subject, would correspond to a VA of 20/20. A representative 13-thread kit would include threads of the following thicknesses: 406 mils, 203 mils, 105.5 mils, 81.2 mils, 71.05 mils, 60.9 mils, 50.75 mils, 40.6 mils, 20.3 mils, 15.225 mils, and 10.15 mils.

Thread length can vary and be adapted to the usage environment. Typical thread lengths range from 4 inches to 24 inches, with lengths of 6 to 10 inches suitable for most uses. The threads for use in the kit and method of the invention can be of a variety of materials, including, but not limited to, nylon, polyester, cotton, wire, hair.

Each of the threads can be affixed to a separate gripping means or, alternatively, at least two of the threads are affixed to a single gripping means. The gripping means optionally comprises a handle adapted to be concealed within a user's hand. The gripping means can comprise a loop or a knob, or other means by which the thread can be easily grasped within the examiner's hand or suspended from a supportive structure. Examples of supportive structures include, but are not limited to, a valance, a rack (similar to a key rack), and a bracket. The gripping means can be made from a variety of materials, including but not limited to, paper, wood, metal, plastic, wire, cord. The gripping means can be designed so that it is suitable for being held in the hand of an examiner while testing a subject, or being suspended from a supportive structure. Alternatively, one can customize the gripping means for one particular mode of use. The gripping means can optionally be the site of a label for identification, either directly with the target VA or with a number, letter or symbol for reference to a corresponding target VA.

In one embodiment, the kit further comprises a valance 30. The valance 30 comprises a concealing face 40 and at least two receiving means 32 affixed to the valance 30 behind the concealing face 40, the receiving means 32 adapted to receive the gripping means 20 at the first end of each of the threads 10, 12, 14 of the plurality, whereby the threads are removably suspended from the valance 30. The receiving means 32 can be hooks, guides, pins, knobs, Velcro® or other means of holding a thread while in use. The valance 30 may include one, two or more receiving means 32. In one embodiment, the valance 30 comprises two receiving means 32, spaced at least a few inches apart. This allows for variation of the receiving means from which a test thread is suspended at any given time. By randomly varying the position from which a test thread is suspended, one can reduce the risk of a subject grabbing or looking at a thread merely by luck without actually seeing the test thread. This can improve the accuracy of determining the limits of a subject's visual acuity.

The valance can be made of any material that is sufficiently sturdy to be held in the hand, mounted on a wall or other surface, or rested on a supporting bracket. Representative materials for the valance include, but are not limited to, wood, plastic, cardboard, metal, Styrofoam®, and the like. The concealing face of the valance is sufficiently opaque that a test subject cannot see whether and where a test thread and/or its gripping means is suspended from the valance.

Method

The invention also provides a method for testing visual acuity in a subject. The method comprises displaying a test thread at a set distance in front of the subject's face, and determining whether the subject grabs or looks at the test thread. The method typically further comprises displaying a subsequent thread at the set distance, and determining whether the subject grabs or looks at the subsequent thread. These steps are repeated using subsequent threads of varying thickness. The set distance is typically 6-20 inches, typically 14 inches.

The test and subsequent threads each has a first end, a second end, and the threads range in thickness between 0.01 mm to 15 mm (or 0.3937-590.55 mils; 1 mm=39.37 mils), wherein the thickness of each of the threads differs from all other threads by at least 0.01 mm, whereby visual acuity is determined by the thickness of the threads the subject is able to grab or look at. In some embodiments, the threads range in thickness between 0.10 mm and 1.5 mm. Optionally, the difference between thread thickness can be at least 0.10 mm.

In some embodiments, the method further comprises obscuring the first ends of the test and subsequent threads. The obscuring can comprise placing a hand over the first end of each thread. Alternatively, the obscuring can comprise suspending the test and subsequent threads from a valance.

In some embodiments, the method further comprises varying, along a horizontal axis, the position of the obscured first ends of the test and subsequent threads. By randomly varying the position from which a test thread is suspended, one can reduce the risk of a subject grabbing or looking at a thread merely by luck without actually seeing the test thread. This can improve the accuracy of determining the limits of a subject's visual acuity. Optionally, the determining step comprises observing whether the subject grabs the threads. Alternatively, the determining step can comprise observing whether the subject looks at the threads. In one embodiment, the test and subsequent threads are each displayed at one of two possible locations, and the observing is performed by an observer who is blind to the location of the threads.

EXAMPLE

The following example is presented to illustrate the present invention and to assist one of ordinary skill in making and using the same. The example is not intended in any way to otherwise limit the scope of the invention.

In this Example, I held an extremely thin thread in front of a one-year-old male subject. It was readily apparent that he saw the thread and he grabbed the thread and held on to it. It was remarkable, as the thread was barely visible to the adult examiner with a VA of 20/20. I made the thread thinner and thinner and he was still able to see it and grasp it. Based on the thickness of these test threads, I was able to conclude that his visual acuity must be as good as 20/20 or better.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A kit for testing visual acuity in a subject comprising:
   (a) a plurality of threads, each of the threads having a first end, a second end and a thickness of 0.01 mm to 15 mm, wherein the thickness of each of the threads differs from all other threads of the plurality by at least 0.01 mm;
   (b) one or more gripping means to which one or more of the threads of (a) is affixed at the first end; and
   (c) instructions for use of the plurality of threads in testing visual acuity in a subject.

2. The kit of claim 1, wherein the plurality of threads comprises at least 5 threads.

3. The kit of claim 1, wherein the plurality of threads comprises at least 10 threads.

4. The kit of claim 1, wherein the plurality of threads consists of 5 to 15 threads.

5. The kit of claim 1, wherein each of the threads is affixed to a separate gripping means.

6. The kit of claim 5, wherein the gripping means comprises a handle adapted to be concealed within a user's hand.

7. The kit of claim 1, wherein at least two of the threads are affixed to a single gripping means.

8. The kit of claim 1, wherein the gripping means comprises a loop or a knob.

9. The kit of claim 8, further comprising a valance, wherein the valance comprises a concealing face and at least two receiving means affixed to the valance behind the concealing face, the receiving means adapted to receive the gripping means at the first end of each of the threads of the plurality, whereby the threads are removably suspended from the valance.

10. The kit of claim 1, wherein the plurality of threads comprises a thread of each of the following thicknesses: 406 mils, 203 mils, 105.5 mils, 81.2 mils, 71.05 mils, 60.9 mils, 50.75 mils, 40.6 mils, 20.3 mils, 15.225 mils, and 10.15 mils.

11. A method for testing visual acuity in a subject, the method comprising:
   (a) displaying a test thread at a set distance in front of the subject's face;
   (b) determining whether the subject grabs or looks at the test thread;
   (c) displaying a subsequent thread at the set distance;
   (d) determining whether the subject grabs or looks at the subsequent thread; and
   (e) repeating steps (c) and (d) using subsequent threads of varying thickness, wherein the set distance is 6-20 inches, wherein the test and subsequent threads each has a first end, a second end, and the threads range in thickness between 0.01 mm to 15 mm, wherein the thickness of each of the threads differs from all other threads by at least 0.01 mm, whereby visual acuity is determined by the thickness of the threads the subject is able to grab or look at.

12. The method of claim 11, further comprising obscuring the first ends of the test and subsequent threads.

13. The method of claim 12, wherein the obscuring comprises placing a hand over the first end of each thread.

14. The method of claim 12, wherein the obscuring comprises suspending the test and subsequent threads from a valance.

15. The method of claim 12, further comprising varying, along a horizontal axis, the position of the obscured first ends of the test and subsequent threads.

16. The method of claim 11, wherein the determining of steps (b) and (d) comprise observing whether the subject grabs the threads.

17. The method of claim 11, wherein the determining of steps (b) and (d) comprise observing whether the subject looks at the threads.

18. The method of claim 17, wherein the test and subsequent threads are each displayed at one of two possible locations, and the observing is performed by an observer who is blind to the location of the threads.

19. The method of claim 11, wherein the set distance is about 14 inches.

20. The method of claim 19, wherein the test thread of step (a) has a thickness of 20.3 mils.

* * * * *